United States Patent [19]

Kindlmann et al.

[11] Patent Number: 5,027,018
[45] Date of Patent: Jun. 25, 1991

[54] HIGH VOLTAGE ELECTROPHORESIS APPARATUS

[75] Inventors: Peter J. Kindlmann, Guilford; Robert A. Valley, Jr., New Haven, both of Conn.

[73] Assignee: Eastman Kodak Company, Rochester, N.Y.

[21] Appl. No.: 244,692

[22] Filed: Sep. 14, 1988

[51] Int. Cl.$^5$ .................. H03K 17/687; H03K 17/60; H03K 17/51; C25B 1/00
[52] U.S. Cl. ................................. 307/571; 307/253; 307/643; 204/182.8; 204/299 R
[58] Field of Search ............ 204/299 R, 182.8, 182.9, 204/180.1; 935/19, 20, 21, 85, 86, 87; 435/6; 307/571, 575, 584, 270, 253, 254, 643

[56] References Cited

U.S. PATENT DOCUMENTS

| | | | |
|---|---|---|---|
| 4,423,341 | 12/1983 | Shelly | 307/570 |
| 4,461,966 | 7/1984 | Hebenstreit | 307/571 |
| 4,473,452 | 9/1984 | Cantor et al. | 204/182.8 |
| 4,511,815 | 4/1985 | Wood | 307/584 |
| 4,692,643 | 9/1987 | Tokunaga et al. | 307/584 |
| 4,694,206 | 9/1987 | Weinberg | 307/571 |
| 4,737,251 | 4/1988 | Carle et al. | 204/182.8 |
| 4,748,351 | 5/1988 | Barzegar | 307/571 |

Primary Examiner—Stanley D. Miller
Assistant Examiner—Trong Quang Phan
Attorney, Agent, or Firm—Quarles & Brady

[57] ABSTRACT

A high voltage switch for use in electrophoresis equipment is described. A solid state switch element is triggered by a continuous DC voltage derived from an isolated and rectified AC trigger signal. The gate of solid state element is connected by a low impedance path to ground when the AC signal ceases.

6 Claims, 3 Drawing Sheets

HIGH VOLTAGE ELECTROPHORESIS APPARATUS

BACKGROUND OF THE INVENTION

This invention relates to electrophoresis equipment and, more particularly, to a method of applying alternating high voltage fields across an electrophoresis medium.

Electrophoretic methods make use of the difference in mobility between charged particles, suspended in a supporting medium and subject to the influence of an electrical field, to separate such particles from one another. The mobility of a charged particle is principally influenced by its charge-to-mass ratio but may be affected by a number of other factors including, importantly, the interference between the migrating particles and the structure of the supporting medium. Particles of similar charge-to-mass ratio may therefore be separated by exploiting the difference in their physical interaction with the support medium, which in turn is chiefly the result of differences in the migrating particles' size and shape.

If the electrical field to which the migrating particles are subjected may be varied, particles with similar charge-to-mass ratio may be separated by yet another means which takes advantage of differences between the particles relative ability to reorient themselves under a fluctuating electrical field.

Carle, et al., International Patent No. PCT/US 86/02038, discusses the separation of DNA molecules with similar charge-to-mass ratio through the use of pulsed or reversing electrical fields along one axis of the supporting medium. Carle, et al., postulate that such molecules, under a uniform field, orient themselves with respect to their migration, so as to have approximately equal mobility despite differences in their length. In an alternating field, however, the longer molecules are unable to adjust their orientation to the changing field as rapidly as the shorter molecules and hence cannot maintain a high mobility orientation. Separation of such molecules is obtained by alternating the electrical field across the supporting medium at the appropriate frequency to accentuate the difference in mobility between the longer and shorter molecules. The time period of one of the two polarities of voltage is adjusted to be longer than that of the reversed polarity insuring a net migration of molecules in one direction. An analogous procedure makes use of switched fields of different voltage rather than different periods.

Carle, et al., also disclose a means of using a pulsed rather than polarity switched electric field to separate certain molecules. Under this approach, the molecular separation results from an intrinsic propensity of the molecule to "relax" into lower mobility configurations in the absence of an applied field. The ability to separate molecules under this approach results from differences in "relaxation" time and reorientation from "relaxation" time between such molecules.

A different technique using alternating electrical fields across a supporting medium is disclosed in Cantor & Schwartz, U.S. Pat. No. 4,473,452 which discusses the application of two transverse alternating electrical fields along a plane of supporting medium. Such transverse fields may be of different voltages and may be varied in their angle to each other and may be pulsed or reversed in polarity.

The practical implementation of all of the above-described modulated field techniques requires one or more power sources that may be switched on and off or reversed in polarity automatically to provide a periodic variation in field intensity across the supporting medium. At the present time, these techniques involve total field voltages of less than several hundred volts and such power sources are constructed of a combination of a DC power supply of correct voltage and current rating in combination with a mechanical or solid state relay of a type commercially available. The relay is then actuated by a lower voltage timing module.

As modulated field electrophoresis techniques are developed, it is believed that voltages of several thousand volts or more will be required in order to realize two benefits. The first benefit of using such high voltages in these techniques is that for a given field gradient (expressed in volts per length of support medium) a higher voltage allows larger separation area which in turn may result in greater separation distances between migrating particles and hence improved resolution. The second benefit of higher electric fields is that the speed of migration of charged particles is approximately proportional to the strength of the gradient and therefore at high voltages the separation process may be greatly accelerated.

Nevertheless, there are significant obstacles to the use of high voltages, the most significant being the difficulty of reliably switching high DC voltages over many cycles. The prior art has made use of mechanical relays and has suggested the use of so called "solid state" relays.

The use of mechanical relays is severely limited in higher voltage applications as a result of increased propensity of higher voltage to arc across relay contacts during each relay cycle. Over many repetitions this arcing pits the relay contacts ultimately causing their failure. The expected lifetime of a mechanical reed relay operated at high voltages and switched once every several seconds may be less than one month. Some field modulated electrophoretic techniques require switching times as fast as once every several milliseconds.

Solid state relays solve the contact wear problem but are generally available only for relatively low voltages. Such solid state relays are typically composed of triggering circuitry, possibly including an optical isolator to allow a "floating voltage" trigger signal, and a solid state switch element, frequently a MOSFET. It should be noted that the commonly available and somewhat higher voltage Triac or SCR based solid state relays are intended for switching alternating currents and require the switched voltage to drop to zero before they will reset. These switches cannot be used in a electrophoresis design where DC voltages must be switched.

Commercially available solid state relays generally cannot be combined or "stacked" to handle higher voltages because of limitations of the driving circuitry. More precisely, the triggering circuitry on most D.C. solid-state relays is voltage referenced to one side of the switch so that if the switches are placed in series, the relay triggering voltage can no longer be precisely determined. Further, because of the tendency of such devices to switch asynchronously, an individual device in a stacked configuration may be subjected to many times its maximum rated voltage.

Solid state relays with "isolated" trigger circuitry may overcome this first obstacle to stacking, that imposed by the referencing of the trigger circuitry to the switch itself, but generally suffer from high trigger circuit impedances. Optically coupled devices are limited by the relatively high impedances of optically sensitive circuitry. Circuits triggered by capacitively or inactively isolated D.C. pulses, where the pulses toggle the relay on and off, are also high impedance circuits as a necessary result of the low energy transferred by a single pulse at practical voltage levels. Further, these pulse triggered circuits are necessarily sensitive to pulse-like capacitively coupled noise. The switching of high voltage fields across a supporting medium, in high voltage modulated field electrophoresis, by definition, involves the rapid switching of high voltages. This switching produces capacitively coupled high amplitude voltage spikes which makes susceptibility to electrical noise particularly acute in these applications. The polarized nature of most solid state switching devices and the need for reversing the polarity of the applied field in modulated field electrophoresis techniques requires that a number of solid state switches be connected to each other. This in turn, increases the possibility that any voltage spikes developed by one switch will be capacitively coupled into the switching trigger circuitry of another switch.

Finally, conventional solid state relays are generally designed to provide the maximum attainable speed of switching transition between the "on" state and the "off" state. This is to reduce the power dissipated in the solid state switching element and thereby increase the average current that may be handled by the device. Unfortunately, such rapid switching speeds increase the amplitude of voltage spikes and thereby increase the chance of false triggering of other switches in an electrophoresis application, and the chance of interference with other sensitive laboratory equipment.

SUMMARY OF THE INVENTION

The present invention relates to a means of reliably switching high voltages for use in modulated field electrophoresis processes. The invention can be used with a microprocessor controlled timing means connected through controlling circuitry to a number of high voltage solid state switches which may selectively connect an external high voltage DC power source across one of several pairs of electrodes.

One advantageous feature of the invention, therefore, is that it provides a reliable means of switching high voltage DC power, in modulated field electrophoresis applications, without the problems of contact failure or mechanical actuator failure attendant to mechanical relays.

The herein described controlling circuitry for the solid state switches produces an AC signal during the entire time that the solid state switch is turned on. This AC signal is rectified and filtered to produce a high current capacity DC triggering voltage which is continuously applied to the gate of the solid state switching device during the device's "on" period. The high current capacity of this continuous DC triggering voltage helps the solid state switch resist being turned off by external, negative voltage spikes. When the DC triggering voltage is not present, a discharge circuit provides a low impedance path to ground from the gate of the solid state switching device to prevent the solid state device from being turned on by positive, external voltage spikes. Such voltage spikes of both polarities are common in modulated field electrophoresis applications where high voltages are commutated by a plurality of switches in close proximity to each other.

Accordingly, another advantageous feature of the invention is that it provides a trigger means for a solid state switch that is resistant to positive and negative high voltage noise spikes resulting from the switch action of adjacent switches in electrophoresis applications.

In order to achieve higher voltages with available, less expensive, lower voltage solid state devices, the devices may be connected in series. In such a configuration, the trigger voltages for each solid state device must be floating, that is, without reference to any voltage outside of the trigger circuitry. The reason for this is that the absolute trigger voltages for each solid state device in series is unknown during the time the device is switching except with respect to the solid state switching device itself. The continuous AC trigger signal provides a means of coupling the trigger through a transformer so that the rectified and filtered DC trigger voltage will be floating. Further, as an added benefit, because the resulting DC trigger voltage has high current capacity, it may serve as a floating power supply for the remainder of the trigger circuitry thus avoiding the need for an additional floating power supply.

It is therefore another advantageous feature of the invention that it provides a means for combining lower voltage, high gain, solid state switching elements to produce a higher voltage switch from readily available lower cost components.

Still further, in the present invention, a series resistor is placed between the DC trigger voltage and the gate of the solid state switching device to slow down the speed of the switching action and, by reducing the rate of change in voltage across the device, thereby reduce the electrical noise produced by the switch itself. A resistor may be used because the DC trigger signal is not a pulse but is a continuously applied DC voltage. Unlike a DC pulse controlled system, in the present invention there is no danger that such a series resistor will sufficiently reduce the energy from the trigger signal so that the switch is unable to turn on.

It is therefore yet another advantageous feature of the invention that it provides a means for switching high voltage, in modulated field electrophoresis techniques, so that the switching speed is limited to reduce the amplitude of generated capacitively coupled voltage spikes that may interfere with other switch triggers or external electronic instrumentation.

The foregoing and other advantages of the invention will appear from the following description. In the description, reference is made to the accompanied drawings which form a part hereof, and in which there is shown by way of illustration a preferred embodiment of the invention. Such embodiment does not necessarily represent the full scope of the invention, however, and reference must be made to the claims herein for interpreting the breadth of the invention.

DESCRIPTION OF THE PREFERRED EMBODIMENT

Figures 1, 2:
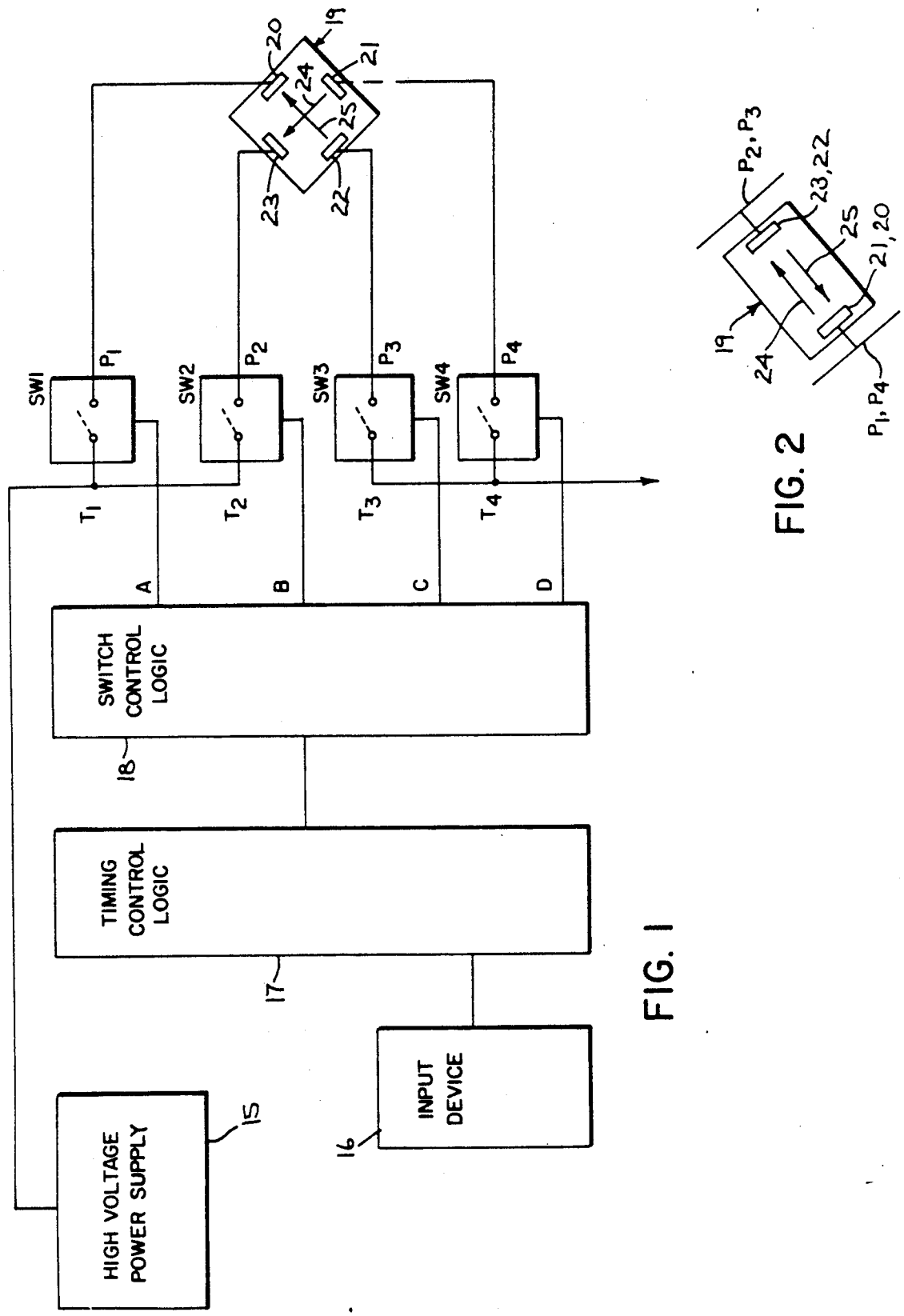
FIG. 1 is a simplified block diagram of a modulated field electrophoresis device showing a cell for experiments involving transverse fields.
FIG. 2 is a schematic representation of an alternate cell configuration for field inversion electrophoretic experiments.

FIG. 1 illustrates, in schematic, a field modulated electrophoresis device incorporating the present invention. A high voltage power supply 15 producing, e.g., 3000 volts DC and several hundred milliamps of current, is connected to one side of two solid state switching elements SW1, and SW2 at points T1 and T2. A generalized electrophoretic cell is shown as 19. Four electrodes 20–23 are shown positioned about the periphery of the cell at 90° increments. The construction of such cells may vary depending on the experiment to be performed as is generally described in prior art, such as, Carle et al. U.S. Pat. No. 4,737,251 and the references cited therein. Electrodes 20 and 23 are connected to point P1 and P2 of respective switches SW1 and SW2 so that each such electrode may be raised to the voltage of the power supply 15 when the respective switch is activated.

In a similar manner, solid state switching elements SW3 and SW4 serve to connect electrodes 21 and 22 to ground when the given switch is actuated. Proper sequencing of switching elements SW1-4 allows alternating electric fields to be established in the plane of the cell as shown by arrows 24 and 25.

Referring to FIG. 2 there is shown an alternate cell design used for field inversion electrophorectic techniques. In this cell design, electrodes 20 and 22 have been electrically joined into a single electrode as have been electrodes 21 and 23. The alternate activation of solid state switches SW1 and SW3, together, and switches SW2 and SW4, together, produces alternating, opposing electric fields 24 and 25 as shown in FIG. 2.

As will be described in more detail below, switch control logic 18 serves to actuate the switches SW1–SW4. This control logic is driven by the timing control logic 17, which may consist of a commercially available sequence timer or programmable controller capable of producing logic level signals. An input device 16 permits reprogramming of the timing control logic 17 by the user.

Figure 3:
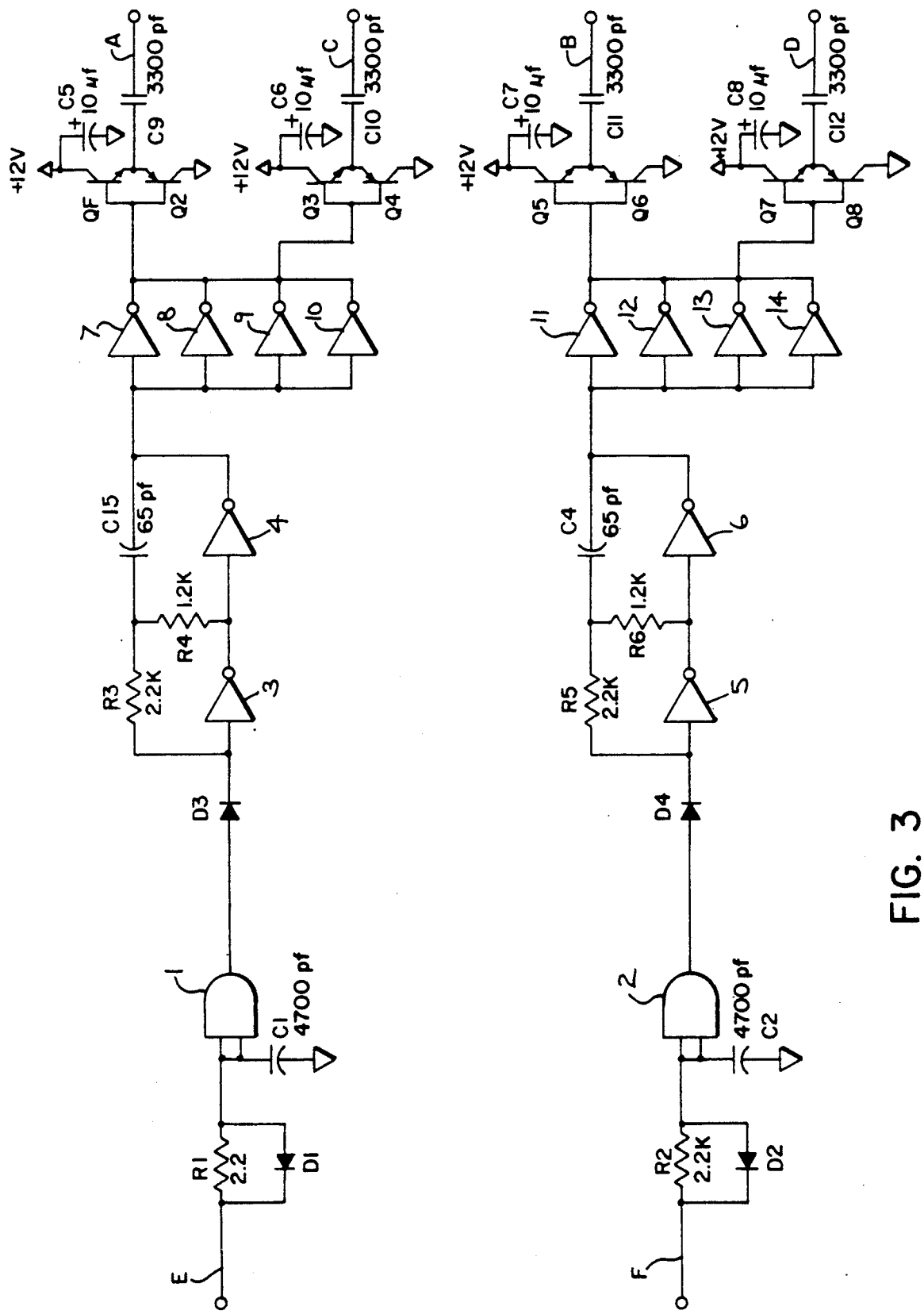
FIG. 3 is a detailed schematic of the switch control logic.

Referring now to FIG. 3, there is shown a detailed schematic of the switch control logic 18 as shown in FIG. 1. Input signals E and F are logic level signals received from the timing control logic 17. When signal E is a logic '1', SW1 and SW3, shown in FIG. 1, are closed. When signal F is a logic '1', SW2 and SW4, also shown in FIG. 1 are closed. Signals E and F and may be activated in any sequence determined by the experimenter subject to the constraint that both E and F may not be simultaneously in the logic "1" state. The circuitry driven by signal F is identical to the circuitry driven by signal E, and although the circuitry for signal E will be described it should be understood that the same description applies to the circuitry for signal F.

Resistor R1 in combination with D1, C1 and Schmitt trigger NAND Gate 1 form a pulse delay circuit which ensures that during the simultaneous transition of signal E to a logic '1' state and signal signal F to a logic "0" state, or vice versa, the outputs of both gate 1 and gate 2 are in a logic '1' state prior to either gate dropping to a logic '0' state. The purpose of this is to ensure that there is no period during which all four switches SW1-4 may be closed thereby short circuiting the high voltage power supply 15. When the signal at point E is in a logical "0" state, current is conducted through D1 discharging capacitor C1. NAND Gate 1 turns off at its switching threshold, which for a CMOS Schmitt trigger is approximately one-third of the power supply voltage. When the signal at point E rises to logical "1", diode D1 is reverse biased and therefore does not conduct and capacitor C1 must charge through resistor R1 to approximately two-thirds of the power supply voltage before gate 1 can turn on. The speed of this charging process and hence the delay in the switching of gate 1 may be adjusted by altering the RC time constant which, in this case, is approximately 10 microseconds.

Accordingly, a logic "1" signal at point E produces a logic "0" signal at the output of NAND Gate 1 which when applied to diode D3, reverse biases D3, effectively disconnecting the output of Gate 1 from inverter Gates 3 and 4 and their associated circuitry. Inverter gates 3 and 4 are logic inverters configured as an oscillator circuit such as that described in RCA publication ICAN-6267 "Astable and Monostable Oscillators Using RCA COS/Mos Digital Integrated Circuits". When the applied signal is low, this oscillator is activated and produces a 2.5 to 3 megahertz square wave, bounded by the logic state voltages, at the output of inverter gate 4.

This high frequency square wave is applied to the inputs of inverter gates 7–10 which are connected in parallel so as to provide increased circuit sourcing and sinking capacity to drive transistors Q1–Q4. Transistor pair Q1 and Q2 and transistor pair Q3 and Q4 are configured as "push-pull" amplifiers to provide further increased current sourcing and sinking capability on the order of several hundred milliamperes. Capacitors C9 and C10 form part of a resonant circuit in connection with the transformer coil primaries TR1-4 to which they connect as will be described further below. Transistor pairs Q1 and Q2 and transistor pair Q3 and Q4 are switched by the same signal but each pair is connected to a different switch SW1 through SW4.

Figure 4:
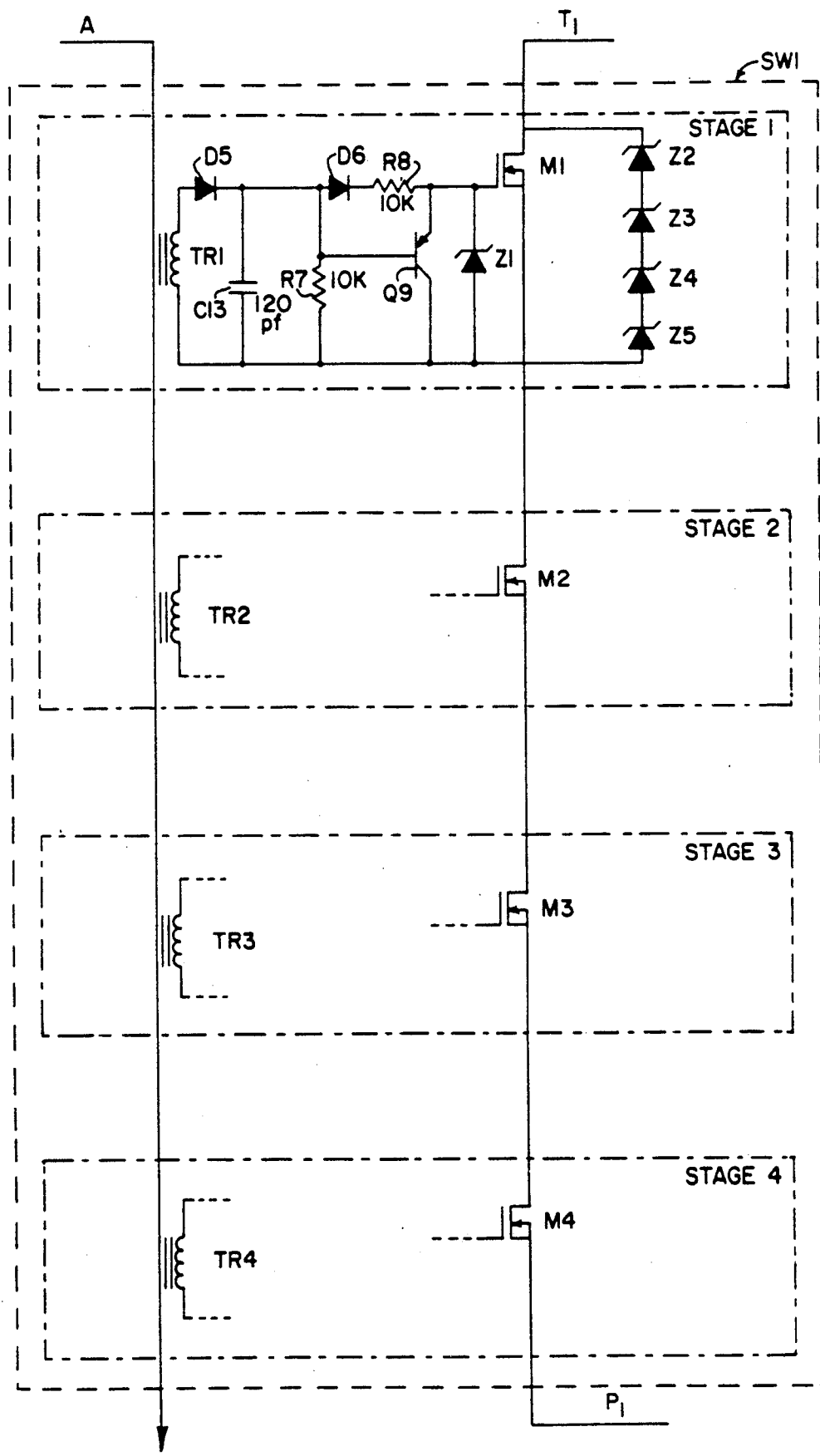
FIG. 4 is a detailed schematic of a representative solid state switch, SW1.

Referring to FIG. 4 there is shown a detailed schematic of solid state switching element SW1. Switching elements SW2-4 are identical in construction with SW1, and therefore, only SW1 will be described. SW1 is composed of four stages each of which is identical and all four of which are connected in series as shown in FIG. 4. Accordingly, only stage 1 will be discussed in detail. The high frequency A.C. signal from transistor pairs Q1 and Q2 of FIG. 3 is connected to stage 1 of switch SW1 at the primary winding of a toroid transformer TR1. The current flowing through the primary of TR1 then flows through the primary of TR2 of stage 2 and TR3 of stage 3 and TR4 of stage 4 before flowing to ground, thereby serving to trigger each of the four stages of switch element SW1 at the same time and in a similar manner. Referring again to the detailed schematic of stage 1, the signal to the primary side of toroid transformer TR1 induces a voltage on TR1's secondary side according to a primary to secondary turns ratio of 1:10. The resulting high frequency signal is applied to D5 and C13 which form a half wave rectifier producing a DC voltage at the junction of D5 and C13. This DC voltage forward biases D6 and current flows through resistor R8 to bias MOSFET M1 into conduction. R8 acting in conjunction with M1's effective capacitance serves to limit the speed with which M1 turns on, and therefore serves to reduce radio frequency noise generated by the turnon of M1. Transistor Q9 is effectively reversed biased because its gate voltage during the turn-on of M1 is at all times higher than or equal to the voltage at its emitter. During the time when M1 is turned on, a high current capacity, low impedance D.C. voltage source is constantly applied to its gate, minimizing the possibility of accidental turn off resulting from coupled noise signals. When the signal at A is turned off the voltage at the junction of D5 and C13 begins to drop, the charge on C13 being conducted through R7. When the voltage at the junction of C13 and R7 drops to approximately seven-tenths of a volt less than the voltage at the junction of R8 and the gate of M1, Q9 is biased into conduction, rapidly discharging any remaining voltage at the gate of M1. Accordingly, M1 is biased off more rapidly than would be the case if its bias voltage were to drop slowly with the decay of the voltage at the junction of C13 and R7. In the off state, the gate of M1 is connected to ground through a low impedance path through Q9 of approximately 100 ohms equivalent resistance.

Zener diode Z1 serves further to protect M1 from capacitively induced voltage spikes resulting from switching of the other switches in the electrophoresis device. Zener diodes Z2-Z5, which each have a breakdown voltage of 200 volts, serve to protect M1 which has a breakdown voltage of 800 volts from potentially damaging voltage in the event that the stages of SW1 switch at slightly different times. When SW1 is off there is no current flowing through line T1. Accordingly, the voltage is equally divided across M1, M2, M3 and M4. When switch 1 is fully turned on the resistance of M1, M2, M3 and M4 is very low and accordingly the total voltage across each switch is on the order of a few tenths of volts to one volt depending on the particular device characteristics and the resistance of the electrophoresis cell. A potential problem arises during the actual switching if one stage switches substantially after the others. If solid state devices M2, M3 and M4 switch prior to M1, M1 would see a full 3000 volts across its terminals absent its protection from diode Z2-5. The presence of diodes Z2-5 ensure that the voltage across terminals of stage 1 will never exceed 800 volts. Voltages above 800 volts will cause diodes 2-5 to conduct for the short period of time necessary for stage 1 to catch up with the other stages. Accordingly, the use of diodes Z2-5 enable the various stages to be placed in series as shown without asynchronous switching between the stages destroying an individual stage MOSFET.

In an alternative embodiment, not shown, additional stages may be added to each switch SW1-4 in order to permit the switching of higher voltages for use in applications such as capillary electrophoresis. The limit to such additional stages is determined primarily by the ability of the switch control logic 18 to drive additional transformer primaries, e.g., in series with TR1-4.

I claim:

1. In a field modulated electrophoresis apparatus comprising a high voltage power supply connected through a solid state switch to at least two electrodes held in an electrophoretic cell, an improved trigger means for said switch comprising:

means for producing an A.C. trigger signal having a start and an end;

a transformer coupled to receive the A.C. trigger signal;

rectifier means connected to the transformer for converting the A.C. trigger signal coupled through said transformer to a D.C. switching voltage said D.C. switching voltage triggering the solid state switch; and a conduction means for discharging the D.C. switching voltage at a predetermined time after the end of the A.C. trigger signal;

so that the solid state switch is turned on at the beginning of the A.C. trigger signal and turned off at the predetermined time after the end of the A.C. trigger signal.

2. The improvement described in claim 1 including a series resistor means interposed between the rectifier means and the switch to reduce the turn-on speed of the switch.

3. In a field modulated electrophoresis apparatus comprising a high voltage power supply connected through a triggerable switch to at least two electrodes in an electrophoretic cell, an improved triggerable switch comprising:

means for producing an AC trigger signal having a start and an end; and a plurality of series connected triggerable stages each comprising:

a series connected solid state switching device a transformer means coupled to receive the AC trigger signal;

a rectifier means for converting the AC trigger signal coupled through said transformer to a D.C. switching voltage said D.C. switching voltage triggering the solid state switching device; and a conduction means for discharging the D.C. switching voltage at a predetermined time after the end of the A.C. trigger signal;

so that each solid state switching device is turned on at the beginning of the A.C. signal and turned off at the predetermined time thereafter.

4. The improvement described in claim 1 including a turn-off assistance circuit means responsive to said D.C. switching voltage and connected to said switch so as to control the speed of turn-off of the switch.

5. The improvement described in claim 4 wherein the turnoff assistance circuit comprises:

a transistor providing a switchable low impedance path to ground from the junction of the rectifier means and the switch so that said transistor is activated by a decrease in the DC switching voltage.

6. The improvement described in claim 1 including a shunting breakdown diode connected in parallel to said switch across said high voltage power supply wherein the reverse breakdown voltage of said breakdown diode is less than or equal to the breakdown voltage of said switch.

* * * * *